United States Patent [19]

Michaelis et al.

[11] 4,279,761

[45] Jul. 21, 1981

[54] MIXTURE OF DI- OR TRITHIOPHOSPHORIC ACID DIESTERS, PROCESSES FOR PRODUCING IT AND ITS USE

[75] Inventors: Klaus P. Michaelis, Lindenfels; Hermann O. Wirth, Bensheim, both of Fed. Rep. of Germany

[73] Assignee: Ciba-Geigy Corporation, Ardsley, N.Y.

[21] Appl. No.: 105,797

[22] Filed: Dec. 20, 1979

Related U.S. Application Data

[62] Division of Ser. No. 871,865, Jan. 24, 1978.

[51] Int. Cl.$^3$ .......................... C10M 1/38; C07F 9/02
[52] U.S. Cl. .................... 252/46.4; 260/953; 260/981; 568/679; 252/46.6; 260/927 R; 260/928; 260/948
[58] Field of Search ................ 260/953, 981, 927 R, 260/928, 948; 568/679; 252/46.6, 46.4

[56] References Cited

U.S. PATENT DOCUMENTS

| | | | |
|---|---|---|---|
| 3,023,209 | 2/1962 | Reese et al. | 260/953 |
| 3,259,579 | 7/1966 | Rogers et al. | 260/953 |
| 3,361,723 | 1/1968 | Ephraim | 260/79 |
| 3,551,152 | 12/1970 | Mackey et al. | 96/85 |
| 3,682,819 | 8/1972 | Morris et al. | 252/32.7 E |
| 3,936,422 | 2/1976 | Wirth et al. | 260/45.95 N |
| 3,988,378 | 10/1976 | Wirth et al. | 260/609 R |

OTHER PUBLICATIONS

CA, 82, 87085w (1975).

*Primary Examiner*—Henry R. Jiles
*Assistant Examiner*—Robert C. Whittenbaugh
*Attorney, Agent, or Firm*—Luther A. R. Hall

[57] ABSTRACT

Mixtures of di- or trithiophosphoric acid diesters produced from 1,2-diols or 1-mercapto-2-hydroxy compounds by reaction with $P_2S_5$ are excellent stabilizing additives for lubricants.

10 Claims, No Drawings

MIXTURE OF DI- OR TRITHIOPHOSPHORIC ACID DIESTERS, PROCESSES FOR PRODUCING IT AND ITS USE

This is a divisional of application Ser. No. 871,865, filed on Jan. 24, 1978, issue fee paid.

The present invention relates to reaction products of optionally mercapto-substituted glycerol ethers and glycerol thioethers, thiolglycerol ethers and thiolglycerol thioethers and monoglycerol esters of di- or trithiophosphoric acid diesters with $P_2S_5$, to processes for producing them, and to their use as stabilising additives for lubricants.

The amine salts of cyclic diesters of dithiophosphoric acids as additives to lubricating oils and fuel oils are described in the German Offenlegungsschrift No. 2,004,154. Although these compounds are effective to a considerable degree, there is still a need to produce similar additives that are even more effective.

The subject matter of the present invention is a mixture of di- or trithiophosphoric acid diesters, which mixture is obtained by the reaction of
(a) compounds of the general formula I, II or III $$R-X-(CH_2-Y-O)_{\overline{n}}H \quad (I)$$
$$(RO)_2P(S)-S-(CH_2-Y-O)_{\overline{n}}H \quad (II)$$

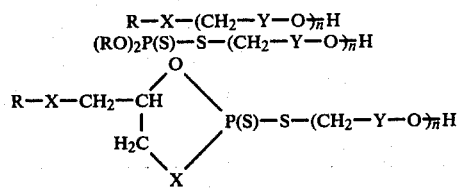
(III)

wherein Y represents the groups

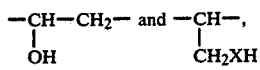

n represents a value from 0.5 to 10, both X's independently of one another represent an oxygen atom or sulphur atom, and R represents a hydrocarbon radical which is optionally interrupted by oxygen or sulphur, and which is of aliphatic or aromatic character, with
(b) phosphorus pentasulphide, and also its metal or ammonium salts, or addition compounds with optionally substituted olefins, alkyl halides or cycloalkyl halides, epoxides and epithio compounds.

Preferably, X in the group

is an oxygen atom, and n represents a value from 0.5 to 4, especially 1 to 2, and particularly 1.

As an aliphatic hydrocarbon radical, R can be linear, and particularly branched, alkyl optionally interrupted by O or S atoms; or cycloalkyl or cycloalkylalkyl optionally substituted by 1 or 2 alkyl groups preferably having 1 to 12 C atoms. As an aromatic hydrocarbon radical, R can be aryl or aralkyl optionally substituted by 1 or 2 alkyl groups. The alkyl contains preferably 1 to 30 C atoms, especially 1 to 24 C atoms, and particularly 1 to 18 C atoms; and the cycloalkyl 5 to 8 ring carbon atoms; it preferably denotes cyclohexyl. Aryl preferably represents phenyl, and aralkyl preferably benzyl; and the cycloalkyl, phenyl or benzyl is preferably substituted with 1 or 2 alkyl groups.

In the formula I, II or III, R represents in particular linear, and especially branched, alkyl having 1 to 24 C atoms, preferably 4 to 18 C atoms.

Examples of R are: methyl, ethyl, propyl, butyl, i-butyl, t-butyl, pentyl, hexyl, 2-methylpentyl, heptyl, octyl, 2-ethylhexyl, nonyl, i-nonyl, decyl, undecyl, dodecyl, 2-ethyldecyl, t-dodecyl, tetradecyl, octadecyl, i-octadecyl, eicosyl, docosyl, tetracosyl, methoxyethyl, methoxy-n-propyl, octoxyethyl, octylthioethyl, cyclopentyl, methylcyclopentyl, ethylcyclopentylmethyl, cyclohexylmethyl, methylcyclohexyl, p-nonylcyclohexyl, cyclododecyl, methylphenyl, ethylphenyl, t-butylphenyl, dimethylphenyl, hexylphenyl, i-octylphenyl, nonylphenyl, dinonylphenyl, dodecylphenyl, methoxyphenyl, methylbenzyl, nonylbenzyl or dodecylbenzyl.

R can also denote radicals of industrial alcohols or alcohol mixtures. These alcohols are generally produced, by the Ziegler process, from aluminium, hydrogen and ethylene, with subsequent hydroxylation, and are usually mixtures of various branched-chain alcohols. These alcohols are obtainable commercially, e.g. Guerbet alcohols and Alfols (manufacturer: Condea), Dobanols (manufacturer: Shell) and Oxanols (manufactuer: Ruhrchemie).

The compounds of the formula I and processes for their production are known; see, e.g., German Auslegerschrift No. 2,234,016, German Offenlegungsschriften Nos. 2,500,315 and 1,930,343, and U.S. Pat. No. 3,361,723.

The aliphatic glycerol ethers are obtained, e.g., most simply by reaction of alcohols with glycidol, in the presence of catalysts, e.g. Lewis acids, such as $BF_3$, $SnCl_4$, $SbF_3$ or $SbF_5$.

The reaction product is a statistical mixture of starting product and monomeric and oligomeric compounds, the composition of the mixture being determined essentially by the reaction conditions and the proportions of the reactants. In the formula I, therefore, n can assume any value from 0.5 to 10. The reaction product can therefore also contain proportions of the alcohol that has been used. This does not necessarily have to be removed. Sometimes, however, it can be advantageous if at least a part of the starting alcohol is removed by distillation.

A further method of obtaining the aliphatic glycerol ethers is by way of the addition products of epichlorohydrin with aliphatic alcohols, such as, e.g.

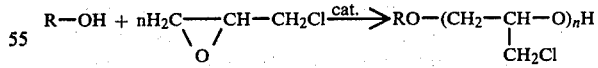

This addition reaction proceeds largely homogeneously, i.e. in the reaction product there is a relatively narrow distribution of a few addition products and scarcely any starting alcohol. The hydrolysis with bases, e.g. sodium hydroxide solution, yields the desired glycide ethers; the reaction with $H_2S$, in the presence of bases as catalysts, yields corresponding monothioglycerol ethers (see U.S. Pat. No. 3,361,723).

Aromatic glycerol ethers are likewise readily obtainable by way of glycidol addition. In this case, however, anionic catalysts, such as sodium hydride or $BF_3$-etherate, can advantageously be used. A relatively homogeneous final product is formed under these conditions.

Under similar conditions as in the case of the phenols, it is possible to obtain the glycerol monothioethers by way of glycidol addition to mercaptans. Relatively homogeneous reaction products are obtained in this case too. The aromatic glycerol ethers and aromatic and aliphatic thioethers are accessible also by way of epichlorohydrin addition.

With regard to purity, the same applies to the compounds of the formulae II and III as applies to the compounds of the formula I.

The compounds of the formula II, which are addition products of glycidol with dithiophosphates, are obtained most simply by reacting 4 mols of alcohol ROH with 1 mol of $P_2S_5$, and then preferably adding 2 mols of glycidol. No catalyst is generally necessary in this case since the epoxide group of the glycidol reacts well with the highly acid PSH group. A relatively homogeneous reaction product is obtained. This reaction is advantageously performed under conditions similar to those for the subsequent production of the mixtures according to the invention, because the successive reaction steps are to be carried out in one vessel.

The compounds of the formula III are obtained preferably by again reacting the mixtures according to the invention, obtained from the reaction of compounds of the formula I with $P_2S_5$, with glycidol, and performing a further reaction with $P_2S_5$.

On reaction of the compounds of the formula I, II or III with phosphorus pentasulphide, there result, with formation of $H_2S$, the compound mixtures according to the invention, which inevitably have essentially the same statistic distribution as the compounds of the formula I, II or III. If these compounds exhibit 1,2-diol structures (for n=1), it can be assumed that in the main cyclic esters are formed, e.g.

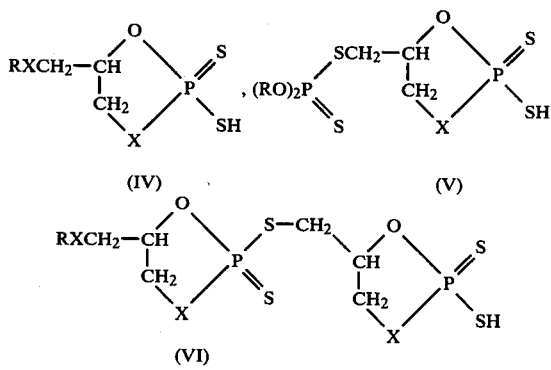

(IV) (V) (VI)

The oligomeric glycerol ethers and thioethers (n>1) contain also free OH and SH groups, respectively, which likewise can react with $P_2S_5$; however, it would scarcely seem likely that cyclic ester groupings form. If the compounds of the formula I still contain parts of starting alcohol, there are formed from these, on reaction with $P_2S_5$, diesters of the type

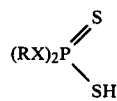

There is used in general in the reaction ¼ mol of phosphorus pentasulphide per mol of OH groups or SH groups in the compounds of the formula I, II or III, and the formed hydrogen sulphide is removed. The reaction can be performed without solvents or in the presence of inert solvents, such as hydrocarbons, e.g. pentane, hexane, petroleum ether, cyclohexane, benzene or toluene, or ethers such as tetrahydrofuran or diethyl ether. Temperatures of 0° to 150° C., preferably 50° to 120° C., are in general used. The $P_2S_5$ is preferably added portionwise or continuously. It is also possible to place $P_2S_5$ into the reaction vessel and to add to it the glycidol ether. During the reaction there are firstly formed diesters of di- or trithiophosphoric acid, so that a highly acid SH group is available for further modifications. With these modifications, for example alkylation or salt formation, the solubility or compatibility with substrates can be improved and volatility reduced, and hence an increase of effectiveness achieved.

Metal salts are obtained by the reaction (neutralisation) with metal bases, e.g. oxides or hydroxides. Particularly suitable metal salts are the barium, cadmium, zinc, antimony, titanium, molybdenum, molybdenyl and tungsten salts.

Preferred salts are however the ammonium salts, which are derived from ammonia or from the primary, secondary and tertiary amines. Also preferred are those amines which promote good solubility in oil. With the combination of starting alcohol of the formula I, II or III and the compound, e.g. an amine, used for the modification, it is possible therefore to obtain, by means of the substituents, e.g. alkyl groups, a good solubility, nonvolatility and compatibility. These salts are produced advantageously by adding phosphorus pentasulphide to the mixture of compounds of the formula I, II or III and an amount of amine necessary for neutralisation. This procedure is carried out preferably in inert solvents and at a temperature of between 20° and 40° C. A further method of production comprises the neutralisation of compound mixtures according to the invention with amines, which can be undertaken after or during formation, e.g. introducing both $P_2S_5$ and amine, and subsequent addition of a glycide ether. It is also possible however to introduce $P_2S_5$ into a mixture of amine and glycide ether.

The amines used for salt formation can correspond to the general formula

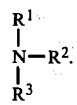

Each of the radicals $R^1$ to $R^3$ independently of one another represents herein a hydrogen atom or a hydrocarbon radical which is optionally interrupted by oxygen or sulphur atoms, which is of aliphatic or aromatic character and which can contain 1 to 30 C atoms, preferably 1 to 18 C atoms. $R^1$, $R^2$ and/or $R^3$ together with the N atom can also form a ring. Examples of hydrocarbon radicals are linear, and particularly branched, alkyl, alkoxyalkyl, alkylthioalkyl, cycloalkyl, cycloalkylalkyl, alkylcycloalkyl, alkylcycloalkylalkyl, aryl, especially phenyl, alkaryl, especially alkylphenyl, aralkyl, especially benzyl and alkaralkyl, particularly alkylbenzyl.

$R^1$ to $R^3$ can also be radicals of industrial amines or mixtures of amines, such as are obtainable commercially, e.g. Primene (manufacturer: Röhm und Haas), Genamine (manufacturer: Hoechst), Adogene (manufacturer: Litachim), or fatty amines, e.g. fatty amines of tall oil, coconut oil, soybean oil or tallow.

Further suitable amines are, e.g., diamines such as alkylenediamines, and bi- and tricyclic diamines such as piperazine or quinuclidine.

Examples of amines are: methylamine, ethylamine, propylamine, butylamine, t-butylamine, hexylamine, octylamine, (2-ethylhexyl)amine, t-octylamine, decylamine, t-dodecylamine, tetradecylamine, octadecylamine, oleylamine, phenylamine, benzylamine, (nonylphenyl)amine, cyclohexylamine, pyridine, piperidine, dimethylamine, methyloctylamine, didoceylamine, ditridecylamine, methyloctyldecylamine, methylcyclohexylamine, phenyloctylamine, trimethylamine, dimethylcyclohexylamine, methyloctyldecylamine, (octoxyethyl)amine, (octylthioethyl)amine, (t-dodecylthioethyl)amine, dodecyldimethylamine, hexadecyldimethylamine, octadecyldimethylamine, tridecyldimethylamine, decyldimethylamine, didodecylmethylamine, methylbutyldodecylamine, dimethylpropylamine, trioctylamine, dioctylmethylamine, dodecylbenzylmethylamine, nonylphenyldimethylamine, phenyldodecylmethylamine, phenyldimethylamine, benzyldimethylamine, allyldibutylamine, methyldodecenylamine, heptadecyldimethylamine, dioctylmethylamine, methyl-$\alpha$-naphthylphenylamine, cyclohexyldimethylamine, nonyldimethylamine, tris(n-tridecyl)amine, tris(n-dodecyl)amine, tris(isooctyl)amine, methylbutylhexadecylamine, triethylamine, 3,5-dimethylpyridine, 2-(ethylhexyl)methyldodecylamine, (methylethyl)-dodecylamine, methylbutyldodecylamine, dimethyldodecylamine, hexadecyldimethylamine, tris(i-dodecyl)amine, dimethylbenzylamine, dimethyl(tert.-octylphenyl)amine, (N-methyl)-1-imidazoline, (N-methyl)-1-pyrrazoline, oxazoline, quinoline, pyrrolidine, N-ethylpyrrolidine, N-methylpiperidine, N-butylpiperidine, thiazole and N-methylphenothiazine.

For modification of the properties, the PSH groups of the mixture according to the invention can be reacted also with optionally substituted olefins, alkyl halides or cycloalkyl halides, preferably the chlorides, epoxides and epithio compounds. These compounds used for modification contain preferably 1 to 30 C atoms, especially 2 to 20 C atoms, and particularly 4 to 18 C atoms.

Examples of olefins are aliphatic olefins having 2 to 20 C atoms, such as ethylene, propylene, butylene, isobutylene, pentylene, hexylene, cyclohexylene, octylene, isooctylene, dodecylene, octadecylene, and substituted olefins such as styrene, methylstyrene, vinyl chloride, vinylidene chloride, vinyl fluoride, acrylonitrile, unsaturated acids, esters or anhydrides, preferably having 1 to 18 C atoms in the ester group, such as acrylic acid, methacrylic acid, maleic acid or fumaric acid, and the alkyl, cycloalkyl, phenyl and benzyl esters, carboxylic acid esters of unsaturated alcohols, such as vinyl alcohol esters, which preferably have 1 to 18 C atoms in the carboxylic acid group, such as vinyl acetate, vinyl propionate, vinyl butyrate, vinyl stearate, vinyl oleate, vinyl benzoate or vinyl maleate, and esters of allyl alcohol as well as vinyl ethers.

Examples of halides are optionally substituted alkyl halides having 1 to 18 C atoms, such as methyl chloride, octyl chloride, dodecyl bromide, octadecyl iodide, benzyl chloride, and hydroxyalkyl halides such as hydroxyethyl chloride. Examples of cycloalkyl are cyclohexyl chloride and cyclopentyl chloride.

Examples of epithio and epoxi compounds are: alkylene oxides and cycloalkylene oxides and -sulphides, such as oxides of ethylene, propylene, butylene, octylene, dodecylene, octadecylene and cyclohexylene, styrene oxide, glycidol, diglycidyl, epichlorohydrin, glycidyl esters, glycidyl ethers and glycidyl thioethers, mono- and polyglycidyl adducts with N-heterocyclic compounds, such as N-glycidylisocyanurate and N,N'-diglycidyl hydantoin. The glycidyl ethers and glycidyl thioethers can contain in the ether group the radical R as defined for the compounds of the formula I.

The compound mixtures according to the invention are effective even in minute amounts a high-pressure additives to lubricants. Thus, mineral and synthetic lubricating oils, and also mixtures thereof, which contain 0.01 to 5% by weight, preferably 0.05 to 3% by weight, relatives to the lubricant, have excellent high-pressure lubricating properties, which are reflected in the greatly reduced wear effects on the parts to be lubricated (EP/AW additive). The lubricants concerned are commonly known to the expert, and are described, e.g., in the "Schmiermittel Taschenbuch" [Lubricant pocket book] (Hüthig Verlag, Heidelberg, 1974). The compound mixtures according to the invention are surprisingly substantially more effective than, for example, the cyclic esters of German Offenlegungsschrift No. 2,004,154, and furthermore they are surprisingly less corrosive.

The lubricating oil can additionally contain other additives which are added to improve certain properties of the basic oil, such as antioxidants, metal-passivating agents, rust inhibitors, agents improving the viscosity index, agents lowering the pour point, dispersants/detergents and other anti-wear additives.

Examples of antioxidants are:
(a) alkylated and non-alkylated aromatic amines and mixtures thereof, e.g.: dioctylphenylamine, mono-t-octylphenyl-$\alpha$- and -$\beta$-naphthylamines, phenothiazine, dioctylphenothiazine, phenyl-$\alpha$-naphthylamine and N,N'-di-sec.-butyl-p-phenyldiamine;
(b) hindered phenols, e.g. 2,6-di-tert.-butyl-p-cresol, 4,4'-bis-(2,6-diisopropylphenyl), 2,4,6-triisopropylphenol, 2,2'-thio-bis-(4-methyl-6-tert.-butyl-phenol), 4,4'-methylene-bis-(2,6-di-t-butylphenol), esters of 3-(3',5'-di-tert.-butyl-4-hydroxyphenyl)-propionic acid and hexane-1,6-diol, thiodiethylene glycol, octanol or pentaerythritol;
(c) alkyl phosphites, aryl phosphites or alkaryl phosphites, e.g.: trinonylphosphite, triphenylphosphite or diphenyldecylphosphite;
(d) esters of thiodipropionic acid or thiodiacetic acid, e.g.: dilaurylthiodipropionate or dioctylthiodiacetate;
(e) salts of carbamic and dithiophosphoric acids, e.g.: antimony-diamyldithiocarbamate, zinc-diamyldithiophosphate, zinc-di-2-ethylhexyl-dithiophosphate or zinc-di-2-methylpropyldithiophosphate;
(f) combinations of two or more antioxidants given above, e.g.: an alkylated amine and a hindered phenol.

Examples of metal-passivating agents are:
(a) for copper, e.g.: benzotriazole, tetrahydrobenzotriazole, 2-mercaptobenzotriazole, 2,5-dimercaptothiadiazole, salicylidenepropylenediamine and salts of salicylaminoguanidine;
(b) for lead, e.g.: sebacic acid, quinizarine and propylgallate;
(c) combination of two or more of the above additives.

Examples of rust inhibitors are:
(a) organic acids, their esters, metal salts and anhydrides, e.g.: N-oleoyl-sarcosine, sorbitan-monooleate, lead naphthenate and dodecenylsuccinic acid anhydride;

(b) nitrogen-containing compounds, e.g.:
I. primary, secondary or tertiary aliphatic or cycloaliphatic amines and amine salts of organic and inorganic acids, e.g. oil-soluble alkylammoniumcarboxylates;
II. heterocyclic compounds, e.g.: imidazolines and oxazolines;

(c) phosphorus-containing compounds, e.g.: amine salts of phosphoric acid partial esters;

(d) sulphur-containing compounds, e.g.: barium-dinonylnaphthalene sulphonates and calcium petroleum sulphonates;

(e) combination of two or more of the above additives.

Examples of agents improving the viscosity index are, e.g.: polymethacrylate, polybutene, olefin copolymers, vinylpyrrolidone and methacrylate copolymers.

Examples of agents lowering the pour point are, e.g.: polymethacrylates and alkylated naphthalene derivatives.

Examples of dispersants/detergents are, e.g.: polybutenylsuccinic acid imides, polybutenylphosphoric acid derivatives, superbasic magnesium, calcium and barium sulphonates and -phenolates.

Examples of other anti-wear additives are, e.g.: compounds containing sulphur and/or phosphorus and/or halogen, such as sulphurised vegetable oils, zinc dialkyldithiophosphates, tritolyl-phosphate, chlorinated paraffins and alkyl- and aryldisulphides.

Examples of foam inhibitors are: silicone oils and polymeric esters.

The following Examples serve to illustrate the invention.

(A) PRODUCTION EXAMPLES

EXAMPLE 1

1.4 mols of glycidol are added dropwise to 1 mol of stearyl alcohol and 1 ml of SnCl$_4$ in such a manner that 75°–80° C. is not exceeded. Stirring is maintained for a further hour at 90°–100° C. to complete the reaction, and the reaction mixture is then allowed to cool. The gel-chromatographical analysis of the product shows approximately the following composition:
stearyl alcohol: 21.8%
stearyl-3-glycerol ether: 31.4%
oligomeric adducts: 46.05%
(polymers): (0.75%)

1 mol of C$_{13}$H$_{27}$NH$_2$ (PRIMENE 81 R) is added to the reaction product, and this mixture is added dropwise, with vigorous stirring, to a suspension, heated to 35° C., of ½ mol of phosphorus pentasulphide in toluene as solvent. Phosphorus pentasulphide goes completely into solution during this reaction and formed H$_2$S escapes. After completion of the reaction, the toluene is removed by vacuum distillation. The compound mixture 1 according to the invention is thus obtained.

EXAMPLE 2

1 mol of i-octyl alcohol and 1 mol of glycidol are reacted according to Example 1. A reaction is then performed with ½ mol of phosphorus pentasulphide until this goes into solution, with toluene not being used in this case. The compound mixture 2 is thus obtained.

EXAMPLES 3 TO 24

The following starting products are reacted in the given molar ratios, in accordance with Example 1, to give the compound mixtures 3–11 and 14 to 24. The compound mixtures 12 and 13 are obtained by reacting the reaction product of Example 2, with heating, with the stated acrylic acid esters.

3: 1 mol of i-octanol + 1 mol of glycidol + ½ mol of P$_2$S$_5$ + 1 mol of t-C$_{13}$H$_{27}$NH$_2$;
4: 1 mol of Oxanol 12/15 (manufacturer: Ruhrchemie) + 1 mol of glycidol + ½ mol of P$_2$S$_5$ + 1 mol of t-C$_{13}$H$_{27}$NH$_2$;
5: 1 mol of laurylmercaptan + 1 mol of glycidol + ½ mol of P$_2$S$_5$ + 1 mol of t-C$_{13}$H$_{27}$NH$_2$;
6: 1 mol of t-laurylmercaptan + 1 mol of glycidol + ½ mol of P$_2$S$_5$ + 1 mol of t-C$_{13}$H$_{27}$NH$_2$;
7: 1 mol of i-octylmercaptan + 1 mol of glycidol + ½ mol of P$_2$S$_5$ + 1 mol of t-C$_{13}$H$_{27}$NH$_2$;
8: 1 mol of

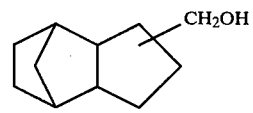

+ 1 mol of glycidol + ½ mol of P$_2$S$_5$ + 1 mol of t-C$_{13}$H$_{27}$NH$_2$;
9: 1 mol of n-dodecanol + 1 mol of glycidol + ½ mol of P$_2$S$_5$ + 1 mol of t-C$_{13}$H$_{27}$NH$_2$;
10: 1 mol of nonylphenol + 1 mol of glycidol + ½ mol of P$_2$S$_5$ + 1 mol of t-C$_{13}$H$_{27}$NH$_2$;
11: 1 mol of Guerbet-16/20 alcohol + 1 mol of glycidol + ½ mol of P$_2$S$_5$ + 1 mol of t-C$_{13}$H$_{27}$NH$_2$;
12: 1 mol of i-octanol + 1 mol of glycidol + ½ mol of P$_2$S$_5$ + 1 mol of methyl acrylate;
13: 1 mol of i-octanol + 1 mol of glycidol + ½ mol of P$_2$S$_5$ + 1 mol of i-octyl acrylate;
14: as 3 but + 1 mol of triethylamine;
15: as 3 but + 1 mol of t-butylamine;
16: as 3 but + 1 mol of ditridecylamine;
17: as 3 but + 1 mol of ethylhexylamine;
18: as 3 but + 1 mol of 4-amino-2,6-di-t-butylphenol;
19: as 3 but + 1 mol of tri-n-octylamine;
20: as 3 but + 1 mol of cyclohexylamine;
21: as 3 but + 1 mol of oleyldihydroxyethylamine;
22: as 3 but + 1 mol of methyldi-i-octylamine;
23: as 3 but + 1 mol of alkylated imidazole (Amin O); and
24: as 3 but + 1 mol of sulphurised oleyldihydroxyethylamine.

EXAMPLES 25 TO 45

37 g (½ mole) of freshly distilled glycidol is added dropwise (without catalyst) at 50°–60° C. to the subsequently listed O,O-dialkyl dithiophosphates (½ mol) (produced from alkanol and P$_2$S$_5$ in toluene), the addition being made in such a manner that the given temperature is not exceeded. The reaction mixture is stirred for one hour at 60° C. and is then allowed to cool. To the solution is added 1 mol of the stated amine, and this mixture is slowly added dropwise at about 40°–45° C. to 56 g of P$_2$S$_5$ in 200 ml of toluene. During this time, a moderate flow of nitrogen is passed through the solution, and the entrained H$_2$S is collected quantitatively in a KOH solution. After the P$_2$S$_5$ has gone completely into solution, within about 2 hours, the toluene is distilled off in vacuo to thus obtain colourless to light-yellow viscous products in quantitative yield.

25: diisooctyl dithiophosphate + t-C$_{13}$H$_{27}$-NH$_2$;
26: diisooctyl dithiophosphate + (t-C$_{13}$H$_{27}$—)$_2$NH;

27: diisopropyl dithiophosphate+t-$C_{13}H_{27}$-$NH_2$;
28: di-dobanol-91 dithiophosphate+ditridecylamine;
29: as 28 but oleylamine;
30: as 28 but amin Adogen 363;
31: as 28 but Amin Adogen 364;
32: as 28 but Amin Adogen 368;
33: as 28 but Amin Primene JMT;
34: diisotridecyl dithiophosphate+ditridecylamine;
35: as 34 but oleylamine;
36: as 34 but Amin Adogen 363;
37: as 34 but Amin Adogen 364;
38: as 34 but Amin Adogen 368;
39: as 34 but Amin Primene JMT;
40: di-dobanol-25 dithiophosphate+ditridecylamine;
41: as 40 but oleylamine;
42: as 40 but Amin Adogen 363;
43: as 40 but Amin Adogen 364;
44: as 40 but Amin Adogen 368;
45: as 40 but Amin Primene JMT.

EXAMPLES 46 TO 50

The alkanols listed below are reacted with glycidol and $P_2S_5$ using the procedure according to Example 1. Without isolation of the product, a further reaction is performed, according to Examples 25-27, with glycidol and thereupon with $P_2S_5$ in the presence of an amine. Colourless to light-yellow viscous products are obtained in quantitative yield.

46: 1 mol of i-octanol+1 mol of glycidol+½ mol of $P_2S_5$+1 mol of glycidol+½ mol of $P_2S_5$+t-$C_{13}H_{27}$-$NH_2$;

47: 1 mol of stearyl alcohol+1 mol of glycidol+½ mol of $P_2S_5$+1 mol of glycidol+½ mol of $P_2S_5$+(t-$C_{13}H_{27}$)$_2$NH;

48: as 46 but (t-$C_{13}H_{27}$)$_2$NH;

49: as 46 but Dobanol-25 alcohol;

50: as 47 but t-dodecylmercaptan instead of stearyl alcohol.

EXAMPLES 51 TO 54

Reaction product from hydroxymercaptans, $P_2S_5$ and amine

To a suspension of ½ mol of $P_2S_5$ in toluene is added dropwise at about 70°-80° C., with vigorous stirring, 1 mol of the hydroxymercaptans given below. Stirring is continued until the $P_2S_5$ has gone completely into solution, in which operation the temperature has not to exceed 120° C. The reaction mixture is afterwards neutralised with the given amine, and the toluene is distilled off in vacuo. There are obtained in quantitative yield colourless to light-yellow liquid products, which are identified by $n_D^{20}$ values.

51: i-$C_8H_{17}OCH_2CH(OH)CH_2SH$+½ mol of $P_2S_5$+Primene JMT ($n_D^{20}$: 1.5140);

52: i-$C_{13}H_{27}OCH_2CH(OH)CH_2SH$+½ mol of $P_2S_5$+Primene JMT ($n_D^{20}$: 1.5108);

53: Dobanol-25-$OCH_2CH(OH)CH_2SH$+½ mol of $P_2S_5$+Primene JMT ($n_D^{20}$: 1.5062);

54: t-$C_{12}H_{25}SCH_2CH(OH)CH_2SH$+½ mol of $P_2S_5$+Primene JMT ($n_D^{20}$: 1.5044).

EXAMPLES 55 TO 62

Addition compounds with epoxy compounds or epithio compounds

The reaction products or the ammonium salts thereof, produced according to Example 2, are reacted at 80°-90° C. with the epoxy or epithio compounds given below. Liquid products are obtained in quantitative yield.

55: 4 i-$C_3H_7OH$+$P_2S_5$+

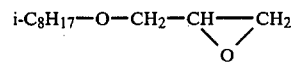

$n_D^{20}$: 1,4819

56: 4 i-$C_3H_7OH$+$P_2S_5$+

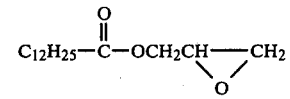

$n_D^{20}$: 1,4882

57: 2 i-$C_8H_{17}$-$OCH_2$-$CHOH$-$CH_2OH$+$P_2S_5$+

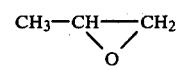

$n_D^{20}$: 1,4910

58: 2 i-$C_8H_{17}$-$OCH_2$-$CHOH$-$CH_2OH$+$P_2S_5$+

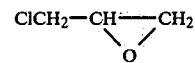

59: 2 i-$C_8H_{17}$-$OCH_2$-$CHOH$-$CH_2OH$+$P_2S_5$+⅓ triglycidylisocyanurate

60: 4 i-$C_8H_{17}OH$+$P_2S_5$+

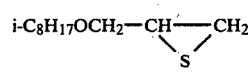

$n_D^{20}$: 1,4922

61: 2 i-$C_8H_{17}OCH_2$-$CHOHCH_2OH$+$P_2S_5$+

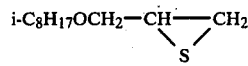

$n_D^{20}$: 1,4980

62: 2 i-$C_8H_{17}OCH_2$-$CHOHCH_2OH$+$P_2S_5$+

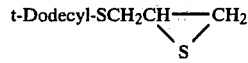

$n_D^{20}$: 1,5175

EXAMPLES 63 TO 65

Addition compounds with olefins. Production according to Examples 55-62

63: 2 i-$C_8H_{17}OCH_2$-$CHOH$-$CH_2OH$+$P_2S_5$+vinyl acetate $n_D^{23}$: 1.5086;

64: 2 i-$C_8H_{17}OCH_2$-$CHOH$-$CH_2OH$+$P_2S_5$+(bis-tridecyl)ammonium acrylate $n_D^{24}$: 1.4931;

65: 2 i-$C_8H_{17}OCH_2$-$CHOH$-$CH_2OH$+$P_2S_5$+ethyl acrylate $n_D^{20}$: 1.5092.

EXAMPLES 66 TO 67

Metal salts

The reaction products produced according to Example 2 are dissolved in toluene, and equimolar amounts of metal acetate are added. The reaction mixture is then refluxed; the formed acetic acid is expelled, and the reaction product is yielded after removal of the toluene.

66: i-$C_8H_{17}OCH_2CHOHCH_2OH + P_2S_5 +$ zinc acetate solid product;

67: i-$C_8H_{17}OCH_2CHOHCH_2OH + P_2S_5 +$ calcium acetate, $n_D^{20}$: 1.4680.

(B) APPLICATION EXAMPLES

The following values were determined with the Shell four-ball apparatus: (tentative method IP 239/69; Extreme pressure and wear lubricant test for oils and greases, four-ball machine).

(1) I.S.L. = initial seizure load; that is the load under which the oil film breaks down within a loading time of 10 seconds;

(2) W.L. = weld load; that is the load under which the 4 balls weld together within 10 seconds;

(3) "scar diameter" in mm; that is the mean diameter of wear after a loading of 70 kg during 1 hour;

(4) the corrosive action in the copper-strip test (Cu-St) was tested in some cases (evaluation scale extends from 1a to 4b).

Catenex 41 (trade name, Shell) was used as the basic oil. The results are given in the following Table.

TABLE

| Compound mixture | Concentration (% by weight) | CU-ST | ISL (kg) | Weld load (kg) | Scar diameter (mm) |
|---|---|---|---|---|---|
| — | — | — | 60 | 160 | 2,42 |
| 1 | 1 | 3b | 135 | 225 | 0,60 |
| 2 | 1 | 2b | — | >200 | 0,9 |
| 3 | 1 | 3b | 135 | 225 | 0,71 |
| 4 | 1 | 3b | 120 | 230 | 0,66 |
| 5 | 1 | 3b | — | >200 | 1,0 |
| 6 | 1 | 3a | — | >200 | 1,0 |
| 7 | 1 | 4a | — | >200 | 1,1 |
| 8 | 1 | 3b | — | >200 | 1,0 |
| 9 | 1 | 4a | — | >200 | 0,8 |
| 10 | 1 | 3b | — | >180 | 0,8 |
| 11 | 1 | 3b | — | >200 | 0,6 |
| 12 | 1 | 2b | — | >200 | 0,4 |
| 13 | 1 | 1b | — | — | 0,4 |
| 26 | 1 | 2a | 100 | 220 | 0,8 |
| 27 | 0.5 | 3 | — | 200 | 0,7 |
| 28 | 1 | 3a | — | >200 | — |
| 29 | 1 | 3a | — | >180 | 0,4 |
| 30 | 1 | 3a | — | >180 | 0,4 |
| 31 | 1 | 3a | — | >180 | 0,4 |
| 32 | 1 | 3a | — | >200 | 0,5 |
| 33 | 1 | 3a | — | >200 | 0,5 |
| 34 | 1 | 2c | — | >200 | — |
| 35 | 1 | 2c | — | >200 | 0,3 |
| 36 | 1 | 2c | — | >180 | — |
| 37 | 1 | 2c | — | >200 | 0,3 |
| 38 | 1 | 2c | — | >180 | 0,4 |
| 39 | 1 | 2c | — | >180 | 0,5 |
| 40 | 1 | 3a | — | >180 | 0,5 |
| 41 | 1 | 3a | — | >200 | 0,3 |
| 42 | 1 | 2c | — | >180 | 0,3 |
| 43 | 1 | 2c | — | >200 | 0,3 |
| 44 | 1 | 3a | — | >200 | 0,4 |
| 45 | 1 | 3a | — | >200 | 0,5 |
| 51 | 1 | 4a | — | >200 | 0,5 |
| 52 | 1 | 4a | — | >180 | 0,4 |
| 53 | 1 | 4a | — | >180 | 0,3 |
| 54 | 1 | 4a | — | >180 | 0,6 |
| 55 | 1 | 1b | — | >200 | 0,5 |
| 56 | 1 | 1b | — | >200 | 0,5 |
| 57 | 1 | 3a | — | >180 | — |
| 58 | 1 | 2b | — | >180 | — |
| 61 | 1 | 3b | — | >200 | 0,4 |
| 62 | 1 | 3b | — | >180 | 0,4 |
| 67 | 0,5 | 2c | — | >180 | 0,5 |

COMPARATIVE TEST

The product 26 and, by way of comparison, commercial EP/AW additives are tested in a basic oil (Flexon 845) in a gear rig according to DIN 51354 until the respective load increment causing damage (SLS) occurs. In this respect, the minimum concentration at which the highest load increment causing damage occurs is determined. The results are given in the following Table.

TABLE

| Product | Concentration (% by weight) | SLS |
|---|---|---|
| 26 | 0,03 | 12 |
| 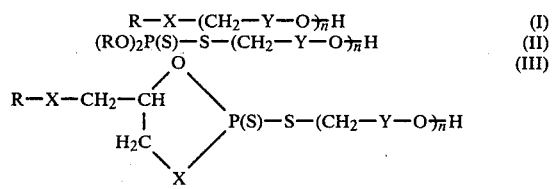 | 0,1 | 12 |
| zinc salt of diisopropyldithiophosphate | 0,5 | 11 |

It is seen that the product according to the invention is the most effective although in the lowest applied concentration.

We claim:

1. The product obtained by the reaction of
(a) a compound of the general formula I, II or III or mixtures thereof $$R-X-(CH_2-Y-O)_{\overline{n}}H \quad (I)$$
$$(RO)_2P(S)-S-(CH_2-Y-O)_{\overline{n}}H \quad (II)$$

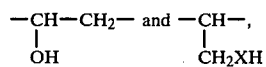
(III)

wherein
y represents the groups $$-\underset{\underset{OH}{|}}{CH}-CH_2- \text{ and } -\underset{\underset{CH_2XH}{|}}{CH}-,$$

n represents a value of 0.5 to 10, both X's independently of one another represents an oxygen atom or sulphur atom, and R represents linear or branched alkyl of 1 to 30 carbon atoms; said alkyl interrupted by oxygen or sulphur; cycloalkyl of 5 to 12 carbon atoms; cycloalkylalkyl of 5 to 12 carbon atoms in the cycloalkyl ring; phenyl; benzyl; or said cycloalkyl, said cycloalkylalkyl, said phenyl or said benzyl substituted by 1 or 2 alkyl groups having 1 to 12 carbon atoms, with (b) phosphorus pentasulfide; in a molar ratio of $\frac{1}{4}$ mol of phosphorus pentasulfide per mole of OH or SH groups of compounds I, II or III, at 0° to 150° C.; said product having free acidic PSH groups formed by the reaction of phosphorus pentasulfide with compounds I, II or III.

2. Product according to claim 1 wherein X represents an oxygen atom.

3. Product according to claim 1 wherein n represents a value of 0.5 to 4.

4. Product according to claim 3 wherein n represents a value of 1 to 2.

5. Product according to claim 1 wherein R represents alkyl of 1 to 24 carbon atoms.

6. Product according to claim 5 wherein R is branched alkyl of 4 to 18 carbon atoms.

7. Product according to claim 1 wherein component (a) consists of a compound of formula I or II.

8. Product according to claim 7 wherein R in formula I or II represents i-octyl, X represents an oxygen atom and n represents 1.

9. Product according to claim 7 wherein component (a) consists of a compound of formula I.

10. A lubricant composition which comprises a mineral oil, a synthetic oil or mixture thereof, and from 0.01 to 5% by weight relevant to the lubricant of a product according to claim 1.

* * * * *